United States Patent
Wu et al.

(10) Patent No.: US 11,555,742 B2
(45) Date of Patent: Jan. 17, 2023

(54) IMAGE GUIDED MICRO-RAMAN SPECTROSCOPY

(71) Applicant: PROVINCIAL HEALTH SERVICES AUTHORITY, Vancouver (CA)

(72) Inventors: Zhenguo Wu, Vancouver (CA); Haishan Zeng, Vancouver (CA); Jianhua Zhao, Vancouver (CA); Liwei Jiang, Vancouver (CA)

(73) Assignee: Provincial Health Services Authority, Vancouver (CA)

( * ) Notice: Subject to any disclaimer, the term of this patent is extended or adjusted under 35 U.S.C. 154(b) by 0 days.

(21) Appl. No.: 17/271,826

(22) PCT Filed: Sep. 4, 2019

(86) PCT No.: PCT/CA2019/051235
§ 371 (c)(1),
(2) Date: Feb. 26, 2021

(87) PCT Pub. No.: WO2020/047660
PCT Pub. Date: Mar. 12, 2020

(65) Prior Publication Data
US 2021/0255041 A1    Aug. 19, 2021

Related U.S. Application Data

(60) Provisional application No. 62/726,746, filed on Sep. 4, 2018.

(51) Int. Cl.
*G01J 3/44*  (2006.01)
*G01J 3/02*  (2006.01)
(Continued)

(52) U.S. Cl.
CPC .......... *G01J 3/4412* (2013.01); *G01J 3/0208* (2013.01); *G01J 3/0218* (2013.01); *G01J 3/0224* (2013.01); *G01J 3/06* (2013.01); *G01J 3/10* (2013.01)

(58) Field of Classification Search
CPC combination set(s) only.
See application file for complete search history.

(56) References Cited

U.S. PATENT DOCUMENTS 4,832,483 A    5/1989   Verma
5,261,410 A   11/1993   Alfano et al.
(Continued)

FOREIGN PATENT DOCUMENTS

WO         9838907 A1      9/1998
WO    WO-02057759 A1 *    7/2002  ........... A61B 5/0068
(Continued)

OTHER PUBLICATIONS

Turner, A. et al., "New class of materials for optical isolators," Appl. Opt. 22, 3152-3154 (1983) (Year: 1983).*
(Continued)

*Primary Examiner* — Dominic J Bologna
*Assistant Examiner* — Roberto Fabian, Jr.
(74) *Attorney, Agent, or Firm* — Oyen Wiggs Green & Mutala LLP

(57) ABSTRACT

Systems for confocal Raman spectroscopy of points of interest or regions of interest with concurrent imaging are disclosed. The imaging may be used for real time selection of points of interest or regions of interest for Raman spectroscopy and to monitor for unwanted motions of a sample while Raman spectra are acquired. Disclosed embodiments apply Reflectance confocal microscopy (RCM) in a confocal Raman spectroscopy system. A single laser may be used as a light source for both RCM and micro-Raman spectroscopy.

(Continued)

A Faraday optical isolator may be applied to extract RCM signals for imaging Systems as described herein have example application for ex vivo sample and in vivo skin measurement.

18 Claims, 9 Drawing Sheets

(51) Int. Cl.
  *G01J 3/06* (2006.01)
  *G01J 3/10* (2006.01)

(56) References Cited

U.S. PATENT DOCUMENTS

| | | | |
|---|---|---|---|
| 5,293,872 A | 3/1994 | Alfano et al. | |
| 5,369,496 A | 11/1994 | Alfano et al. | |
| 6,205,354 B1 | 3/2001 | Gellermann et al. | |
| 6,485,413 B1 | 11/2002 | Boppart et al. | |
| 9,687,152 B2* | 6/2017 | Zeng | G02B 21/0076 |
| 2005/0070791 A1* | 3/2005 | Edney | G01B 9/02088 356/450 |
| 2010/0067102 A1* | 3/2010 | Yokoi | G01N 21/6458 359/385 |
| 2010/0207036 A1* | 8/2010 | Massonneau | A61B 5/0059 250/459.1 |
| 2012/0259229 A1 | 10/2012 | Wang et al. | |
| 2017/0156605 A1* | 6/2017 | Nakao | A61B 5/0261 |

FOREIGN PATENT DOCUMENTS

| | | | | |
|---|---|---|---|---|
| WO | 2004051242 A1 | 6/2004 | | |
| WO | WO-2004070368 A1 * | 8/2004 | | A61B 5/0059 |
| WO | WO-2015075084 A1 * | 5/2015 | | G01J 3/0227 |

OTHER PUBLICATIONS

Zhang, W. et al. "Polarization bandpass filter based on one-dimensional photonic crystal heterostructures," J. Opt. Soc. Am. B 26, 1845-1851 (2009) (Year: 2009).*

Patil, C. et al., "A handheld laser scanning confocal reflectance imaging-confocal Raman microspectroscopy system," Biomed. Opt. Express 3, 488-502 (2012) (Year: 2012).*

Abigail, S. H, et al., "In vivo Margin Assessment during Partial Mastectomy Breast Surgery Using Raman Spectroscopy", Cancer Res 2006, 66:3317-3322.

Bakker Schut, T. C. et al., "In Vivo Detection of Dysplastic Tissue by Raman Spectroscopy", Anal Chem 2000, 72:6010-6018.

Caetano, L. D. V. N. et al., "In vivo confocal Raman spectroscopy for intrinsic aging and photoaging assessment", J Dermatol Sci, 88 (2017) 199-206.

Caspers, P.J. et al., "Automated depth-scanning confocal Raman microspectrometer for rapid in vivo determination of water concentration profiles in human skin", J Raman Spectrosc 2000, 31:813-818.

Caspers, P. J. et al., "Monitoring the Penetration Enhancer Dimethyl Sulfoxide in Human Stratum Corneum in Vivo by Confocal Raman Spectroscopy", Pharm Res 2002, 19:1577-1580.

Caspers, P. J. et al., "In vivo Confocal Raman Microspectroscopy of the Skin: Noninvasive Determination of Molecular Concentration Profiles", J Invest Dermatol 2001, 116:434-442.

Caspers, P. J. et al., "Combined In Vivo Confocal Raman Spectroscopy and Confocal Microscopy of Human Skin", Biophys J 2003, 85:572-580.

Chan, J. W. et al., "Micro-Raman Spectroscopy Detects Individual Neoplastic and Normal Hematopoietic Cells", Biophys J, 90 (2006) 648-656.

Deinum, G. et al., "Histological Classification of Raman Spectra of Human Coronary Artery Atherosclerosis Using Principal Component Analysis", Appl Spectrosc 1999, 53:938-942.

Guze, K. et al., "Parameters defining the potential applicability of Raman spectroscopy as a diagnostic tool for oral disease", J. Biomed. Opt. 2009, 14: 0140161-9.

Hanlon, E. B. et al., "Prospects for in vivo Raman spectroscopy", Physics in Medicine and Biology 2000, 45:R1-R59.

Huang, Z. et al., "Integrated Raman spectroscopy and trimodal wide-field imaging techniques for real-time in vivo tissue Raman measurements at endoscopy", Opt. Lett. 2009, 34:758-760.

Huang, Z. et al., "Near-infrared Raman spectroscopy for optical diagnosis of lung cancer", Int. J. Cancer 2003, 107:1047-1052.

Huang, Z. et al., "Raman Spectroscopy in Combination with Background Near-infrared Autofluorescence Enhances the In Vivo Assessment of Malignant Tissues", Photochem Photobiol 2005, 81:1219-1226.

Huang, Z. et al., "Raman spectroscopy of in vivo cutaneous melanin", J of Biomed Opt 2004, 9:1198-1205.

Huang, Z. et al., "Rapid near-infrared Raman spectroscopy system for real-time in vivo skin measurements", Opt Lett 2001, 26:1782-1784.

Koljenovic, S. et al. "Raman microspectroscopic mapping studies of human bronchial tissue", J. Biomed. Opt. 2004, 9:1187-1197.

Lieber, C. A. et al., "In Vivo Nonmelanoma Skin Cancer Diagnosis Using Raman Microspectroscopy", Laser Surg Med 2008, 40(7):461-467.

Lieber, C. A. et al., "Raman microspectroscopy for skin cancer detection in vitro", J Biomed Opt, 13 (2008) 024013-024013-024019.

Lopes, M. B. et al., "In vivo Confocal Raman Spectroscopic Analysis of the Effects of Infrared Radiation in the Human Skin Dermis", Photochem Photobiol, 93 (2017) 613-618.

Lui, H. et al., "Real-time Raman Spectroscopy for In Vivo Skin Cancer Diagnosis", Cancer Res, 72 (2012) 2491-2500.

Magee, N. D. et al., "Ex Vivo Diagnosis of Lung Cancer Using a Raman Miniprobe", Journal of Physical Chemistry B 2009, 113:8137-8141.

Mahadevan-Jansen, A. et al., "Raman spectroscopy for the detection of cancers and precancers", J Biomed Opt 1996, 1, 31-70.

Mahadevan-Jansen, A. et al., "Near-Infrared RamanSpectroscopy for In Vitro Detection of Cervical Precancers", Photochem Photobiol 1998, 68:123-132.

McGregor, H. C. et al., "Real-time endoscopic Raman spectroscopy for in vivo early lung cancer detection", Journal of Biophotonics, 2017, 10: 98-110.

Molckovsky, A. et al., "Diagnostic potential of near-infrared Raman spectroscopy in the colon: differentiating adenomatous from hyperplastic polyps", Gastrointest Endosc 2003, 57:396-402.

Movasaghi, Z. et al., "Raman Spectroscopy of Biological Tissues", Applied Spectroscopy Reviews 2007, 42:493-541.

Nazemi, J. H. et al., "Lipid concentrations in human coronary artery determined with high wavenumber Raman shifted light", J. Biomed. Opt. 2009, 14(3):0340091-6.

Patil, C.A. et al., "A handheld laser scanning confocal reflectance imaging-confocal Raman microspectroscopy system", Biomed. Opt. Express, 3 (2012) 488-502.

Percot, A. et al., "Direct Observation of Domains in Model Stratum Corneum Lipid Mixtures by Raman Spectroscopy", Biophysical Journal 2001, 81:2144-2153.

Piredda, P. et al., "Subcellular Raman Microspectroscopy Imaging of Nucleic Acids and Tryptophan for Distinction of Normal Human Skin Cells and Tumorigenic Keratinocytes", Anal Chem, (2015).

Rajadhyaksha, M. et al., "In Vivo Confocal Scanning Laser Microscopy of Human Skin II: Advances in Instrumentation and Comparison With Histology", J Invest Dermatol 1999, 113:293-303.

Robichaux-Viehoever, A. et al., "Characterization of Raman Spectra Measured in Vivo for the Detection of Cervical Dysplasia", Appl. Spectrosc. 2007, 61 pp. 986-997.

Shafer-Peltier, K.E. et al., "Raman microspectroscopic model of human breast tissue: implications for breast cancer diagnosis in vivo", J Raman Spectrosc, 33 (2002) 552-563.

(56) References Cited

OTHER PUBLICATIONS

Shim, M. G. et al., "Study of Fiber-Optic Probes for in Vivo Medical Raman Spectroscopy", Applied Spectroscopy 1999, 53: 619-627.

Short, M. A. et al., "Development and preliminary results of an endoscopic Raman probe for potential in vivo diagnosis of lung cancers", Opt Lett 2008, 33(7):711-713.

Silveira Jr., L. et al., "Correlation Between Near-Infrared Raman Spectroscopy and Histopathological Analysis of Atherosclerosis in Human Coronary Arteries", Lasers Surg Med 2002, 30:290-7.

Stone, N. et al., "Near-infrared Raman spectroscopy for the classification of epithelial pre-cancers and cancers", J Raman Spectrosc 2002, 33:564-573.

Teixeira, A. P. et al., "Confocal Raman spectroscopy: determination of natural moisturizing factor profile related to skin hydration", Revista Brasileira de Engenharia Biomedica, 30 (2014) 11-16.

Tu, A. T., Raman Spectroscopy in Biology: Principles and Applications New York, NY: Wiley; 1982.

Uzunbajakava, N. et al., "Nonresonant Confocal Raman Imaging of DNA and Protein Distribusion in Apoptotic Cells", Biophys J, 84 (2003) 3968-3981.

Wang, H. et al., "Depth-resolved in vivo micro-Raman spectroscopy of a murine skin tumor model reveals cancer-specific spectral biomarkers", J Raman Spectrosc, 42 (2011) 160-166.

Wang, H. et al., "A Method for accurate in vivo micro-Raman spectroscopic measurements under guidance of advanced microscopy imaging", Sci. Rep., 3 (2013).

Yamazaki, H. et al., "The diagnosis of lung cancer using 1064-nm excited near-infrared multichannel Raman spectroscopy", Radiation Medicine 2003, 21:1-6.

Zhao, J. et al., "Integrated real-time Raman system for clinical in vivo skin analysis", Skin Research and Technology, 14 (2008) 484-492.

Zoladek, A. et al., "Non-invasive time-course imaging of apoptotic cells by confocal Raman micro-spectroscopy", J Raman Spectrosc, 42 (2011) 251-258.

Wu, Z. et al., "Precise in vivo tissue micro-Raman spectroscopy with simultaneous reflectance confocal microscopy monitoring using a single laser", Optics Letters 2019, 44(6):1383-1386.

Erdogan, T., Semrock Technical Note Series: A New Class of Polarization Optics Designed Specifically for Lasers, 2019.

\* cited by examiner

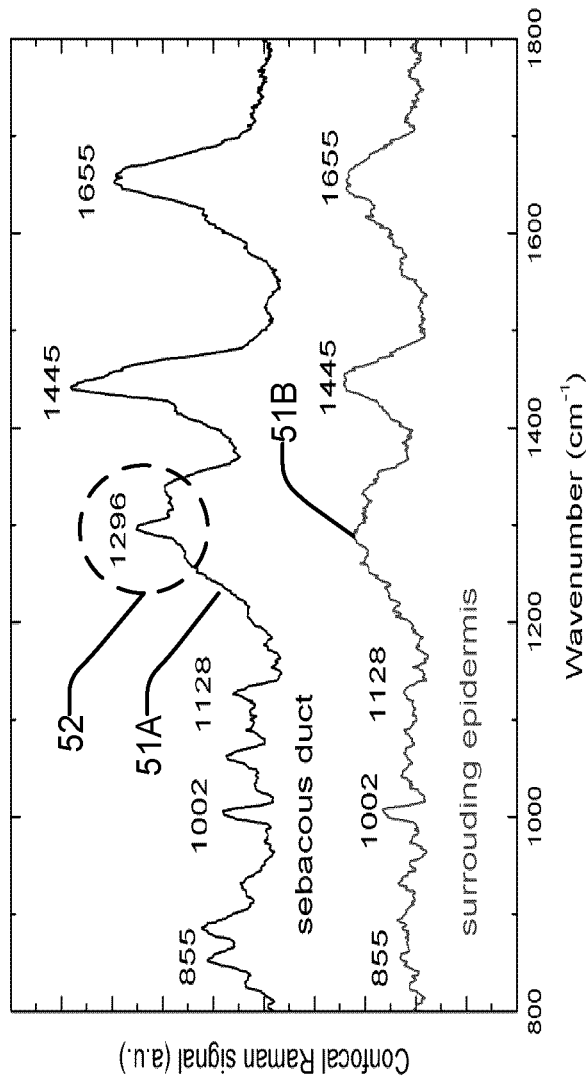
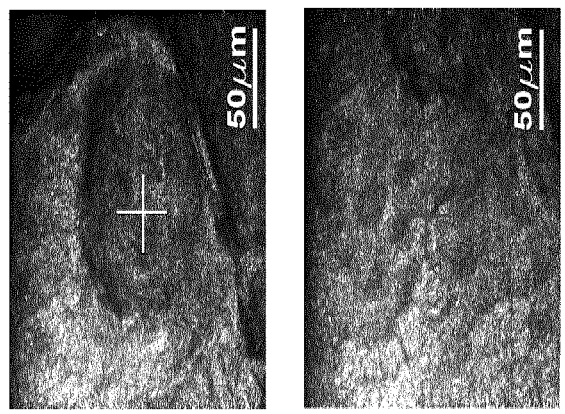
FIG. 4A
FIG. 4B
FIG. 4C

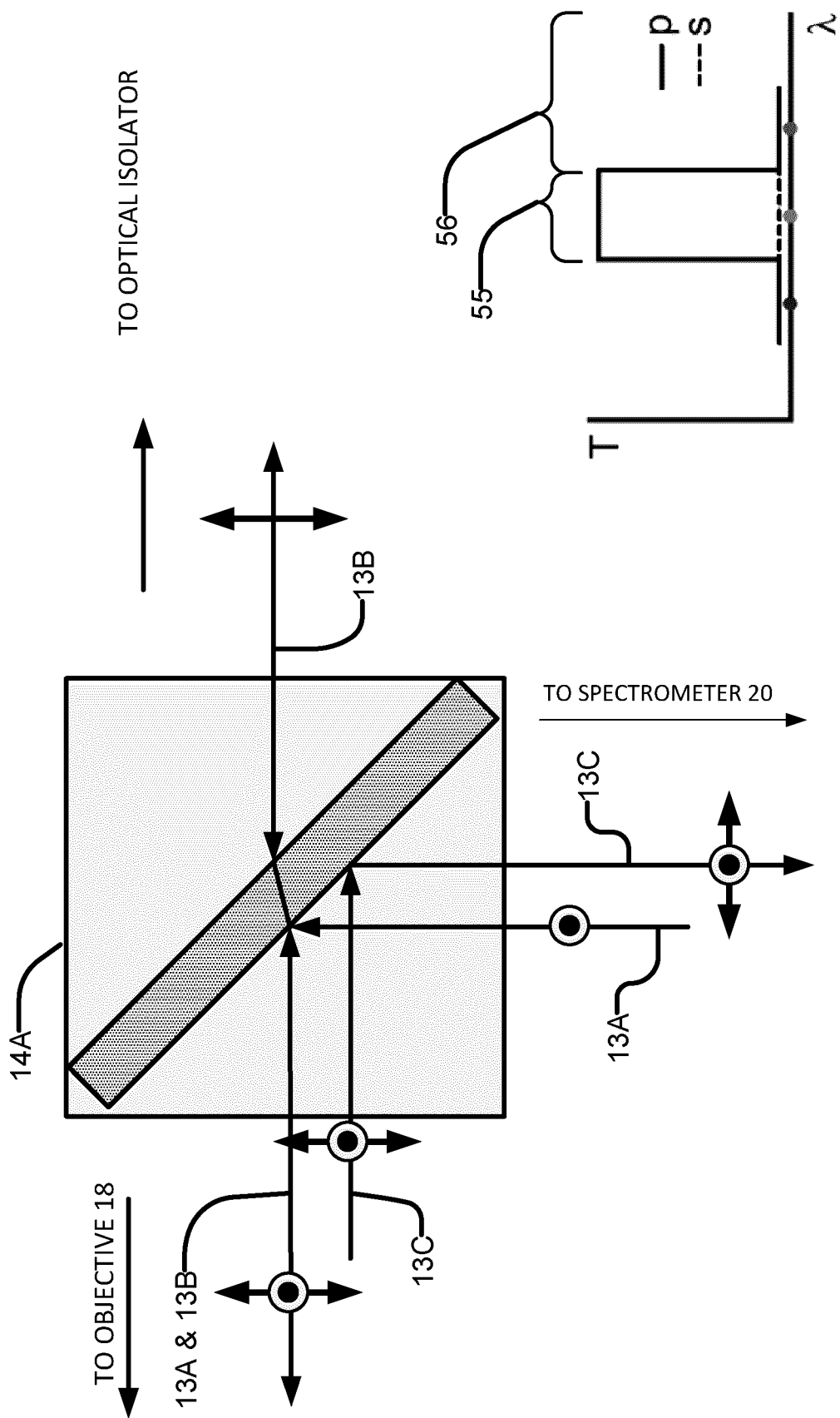

IMAGE GUIDED MICRO-RAMAN SPECTROSCOPY

CROSS-REFERENCE TO RELATED APPLICATIONS

This application claims priority from U.S. application No. 62/726,746 filed 4 Sep. 2018 and entitled MICRO-RAMAN SPECTROSCOPY WITH SIMULTANEOUS REFLECTANCE CONFOCAL MICROSCOPY MONITORING USING A SINGLE LASER which is hereby incorporated herein by reference for all purposes. For the purposes of the United States of America, this application claims the benefit under 35 U.S.C. § 119 of U.S. application No. 62/726,746 filed 4 Sep. 2018 and entitled MICRO-RAMAN SPECTROSCOPY WITH SIMULTANEOUS REFLECTANCE CONFOCAL MICROSCOPY MONITORING USING A SINGLE LASER which is hereby incorporated herein by reference for all purposes.

FIELD

Cancer of various types is a major cause of mortality and poor health. Detecting locations of tissue abnormalities such as cancer and pre-cancer is an important step in improving outcomes for patients affected by many forms of cancer. A wide range of techniques have been explored with the goal of finding effective and efficient ways to identify abnormal tissues.

One promising technique for characterizing tissues is Raman spectroscopy. Raman spectroscopy may be used to study a tissue by directing light at the tissue. Some of the light scatters inelastically from the tissue. Inelastic interactions with the tissue specimens can cause the scattered light to have wavelengths that are shifted relative to the wavelength of the incident light (Raman shift). The wavelength spectrum of the scattered light (the Raman spectrum) contains information about the nature of the tissue. Raman peaks are typically narrow and in many cases can be attributed to the vibration of specific chemical bonds (or normal modes dominated by the vibration of a functional group) in a molecule. As such, a Raman spectrum provides a "fingerprint" for the presence of various molecular species. Analysis of the Raman spectrum can provide detailed biochemical information about the tissue. Raman spectroscopy can be used for both qualitative identification and quantitative determination of molecular species.

Some Raman spectroscopy techniques provide very high spatial resolution. For example, confocal Raman spectroscopy (CRS) can provide molecular fingerprint information with high spatial resolution. CRS has been widely used in life science research for cancer detection, skin evaluation, cellular biochemistry and other applications.

Raman scattered light is typically relatively faint. When monochromatic light strikes a sample, almost all the observed light is scattered elastically (Rayleigh scattering) with no change in energy (or wavelength). Only a very small portion of the scattered light, typically approximately 1 part in $10^8$, is inelastically scattered (Raman scattering). For this reason, acquiring a Raman spectrum for tissue at a particular point is usually quite slow. For example, obtaining a Raman spectrum often takes at least several seconds.

Unlike other techniques (e.g. magnetic resonance imaging (MRI), x-ray imaging, computed tomography (CT) scanning or photographic imaging) point based techniques such as CRS cannot quickly interrogate a large volume of tissue or a large area of a tissue surface. Since it is generally not practical to survey large areas of tissue using CRS or other point-based techniques, especially for in vivo applications, there is a need for ways to identify which points to interrogate using CRS. This is especially the case where the tissues to be studied are inside the body (e.g. in passages within the lungs or other organs).

P. Caspers, et al., Biophys J, 85 (2003) 572-580 and C. A. Patil, et al., Biomed. Opt. Express, 3 (2012) 488-502 describe systems integrate CRS with reflectance confocal microscopy (RCM). In these systems, images obtained using RCM may be used to identify locations for performing CRS. These systems do not allow CRS and RCM to be performed at the same time. With these systems, RCM can be used to identify a location (i.e. a point of interest or "POI") for performing CRS. The RCM imaging is then turned off and CRS is acquired from the predetermined point of interest.

For systems in which RCM and CRS do not work simultaneously one cannot use RCM images to ensure that all of the acquired Raman signal originates from a microstructure (or microstructures) at the same POI. This is because CRS requires relatively long Raman acquisition time during which it is not possible to tell where the Raman signal is coming from (since RCM is turned off). Involuntary tissue movements can move the POI away from the point at which the Raman spectrum is being acquired.

H. Wang, et al., Sci. Rep., 3 (2013) describes a system developed by researchers at the BC Cancer Research Centre in Vancouver Canada. This system permits acquisition of a Raman spectrum together with RCM. However, the Raman spectrum is obtained for the whole region of interest being viewed using RCM. This system did not permit acquisition of a Raman spectrum from a point of interest while viewing the surrounding area that includes the point of interest using RCM. For higher resolution confocal Raman of fine structures, point of interest measurement is preferred.

The patent literature includes references to the use of Raman spectroscopy for studying tissues including:
a) Verma U.S. Pat. No. 4,832,483 which discloses a method for using Raman spectroscopy for the detection of cancers.
b) Alfano et al. U.S. Pat. No. 5,293,872 which relates to methods which include the use of Raman spectroscopy for distinguishing between calcified atherosclerotic tissue and fibrous atherosclerotic tissue.
c) Alfano et al. U.S. Pat. No. 5,261,410 which discloses a method for using Raman spectroscopy for determining whether a tissue is a malignant tumour tissue, a benign tumour tissue or a normal tissue.
d) Alfano et al. U.S. Pat. No. 5,369,496 which discloses the use of back-scattered light for evaluating tissue samples.
e) Puppels et al. WO 2004/051242 which discloses the use of high-wavenumber Raman spectroscopy for detecting abnormalities in tissue.
f) Boppart et al. U.S. Pat. No. 6,485,413 which discloses an instrument which can be used for collecting various spectra including fluorescence spectra and Raman spectra.

The use of Raman spectroscopy in the study of tissues is described in the following references:
a) Gaspers P J, et al. *Raman spectroscopy in biophysics and medical physics*. Biophys J 2003; 85:572-580;
b) Huang Z, et al. *Rapid near-infrared Raman spectroscopy system for real- time in vivo skin measurements*. Opt Lett 2001; 26:1782-1784;
c) Short M A, et al. *Development and preliminary results of an endoscopic Raman probe for potential in vivo diagnosis of lung cancers*. Opt Lett 2008; 33(7):711-713;

d) Huang Z, et al. *Raman spectroscopy of in vivo cutaneous melanin*. J of Biomed Opt 2004; 9:1198-1205;
e) Huang Z, et al. *Raman Spectroscopy in Combination with Background Near-infrared Auto fluorescence Enhances the In Vivo Assessment of Malignant Tissues*. Photochem Photobiol 2005; 81:1219-1226;
f) Molckovsky A, et al. *Diagnostic potential of near-infrared Raman spectroscopy in the colon: differentiating adenomatous from hyperplastic polyps*. Gastrointest Endosc 2003; 57:396-402;
g) Abigail S H, et al. *In vivo Margin Assessment during Partial Mastectomy Breast Surgery Using Raman Spectroscopy*. Cancer Res 2006; 66:3317-3322;
h) Rajadhyaksha M, et al. *In Vivo Confocal Scanning Laser Microscopy of Human Skin II: Advances in Instrumentation and Comparison With Histology*. J Invest Dermatol 1999; 113:293-303;
i) Lieber C A, et al. *In vivo nonmelanoma skin cancer diagnosis using Raman microspectroscopy*. Laser Surg Med 2008; 40(7):461-467.
j) Tu A T. *Raman spectroscopy in biology: principles and applications* New York, NY: Wiley; 1982;
k) Hanlon E B, et al. *Prospects for in vivo Raman spectroscopy* Physics in Medicine and Biology 2000; 45:R1-R59;
l) Robichaux-Viehoever A, et al. *Characterization of Raman spectra measured in vivo for the detection of cervical dysplasia*. Appl. Spectrosc. 2007; 61 pp. 986-997;
m) Guze K, et al. *Parameters defining the potential applicability of Raman spectroscopy as a diagnostic tool for oral disease*. J. Biomed. Opt. 2009; 14: 0140161-9;
n) Huang Z, et al. *Integrated Raman spectroscopy and trimodal wide-field imaging techniques for real-time in vivo tissue Raman measurements at endoscopy*. Opt. Lett. 2009; 34:758-760;
o) Huang Z, et al. *Near-infrared Raman spectroscopy for optical diagnosis of lung cancer*. Int. J. Cancer 2003; 107:1047-1052;
p) Magee N D, et al. *Ex Vivo diagnosis of lung cancer using a Raman miniprobe*. Journal of Physical Chemistry B 2009; 113:8137-8141;
q) Short M A, et al. *Development and preliminary results of an endoscopy Raman probe for potential in-vivo diagnosis of lung cancers*. Optics Letters 2008; 33(7):711-713;
r) Shim M G, et al. *Study of fiber optic probes for in vivo medical Raman spectroscopy*. Applied Spectroscopy 1999; 53: 619-627;
s) Yamazaki H, et al. *The diagnoses of lung cancer using 1064 nm excited near-infrared multichannel Raman spectroscopy*. Radiation Medicine 2003; 21:1-6;
t) Nazemi J H, et al. *Lipid concentrations in human coronary artery determined with high wavenumber Raman shifted light*. J. Biomed. Opt. 2007; 14(3):0340091-6;
u) Koljenovi'c S, et al. *Raman microspectroscopic mapping studies of human bronchial tissue*. J. Biomed. Opt. 2004; 9:1187-1197;
v) Movasaghi Z, et al. *Raman spectroscopy of biological tissues. Applied Spectroscopy* Reviews 2007; 42:493-541;
w) Percot, A. et al. *Direct observation of domains in model stratum corneum lipid mixtures by Raman spectroscopy*. Biophysical Journal 2001; 81:2144-2153;
x) Mahadevan-Jansen A, and Richards-Kortum R. *Raman spectroscopy for the detection of cancers and precancers*, J Biomed Opt 1996; 1, 31-70;
y) Mahadevan-Jansen A, et al. *Near-infrared Raman spectroscopy for in vitro detection of cervical precancers* Photochem Photobiol 1998; 68:123-132;
z) Bakker Schut T C et al. *In vivo detection of dysplastic tissue by Raman spectroscopy* Anal Chem 2000; 72:6010-6018;
aa) Stone N, et al. *Near-infrared Raman spectroscopy for the classification of epithelial pre-cancers and cancers*, J Raman Spectrosc 2002; 33: 564-573;
bb) Deinum G, et al., *Histological classification of Raman spectra of human coronary artery atherosclerosis using principal component analysis*, Appl Spectrosc 1999; 53:938-942;
cc) Silveira L Jr et al., *Correlation between near-infrared Raman spectroscopy and histopathological analysis of atherosclerosis in human coronary arteries*, Lasers Surg Med 2002; 30:290-7;
dd) McGregor. et al. *Real-time endoscopic Raman spectroscopy for in vivo early lung cancer detection*, Journal of Biophotonics, 2017; 10: 98-110;
ee) H. Lui, et al., Cancer Res, 72 (2012) 2491-2500;
ff) C. A. Lieber, et al., J Biomed Opt, 13 (2008) 024013-024013-024019;
gg) K. E. Shafer-Peltier, et al., J Raman Spectrosc, 33 (2002) 552-563;
hh) H. Wang, et al., J Raman Spectrosc, 42 (2011) 160-166;
ii) P. J. Caspers, et al., J Invest Dermatol, 116 (2001) 434-44;
jj) A. P. Teixeira, et al., Revista Brasileira de Engenharia Biomédica, 30 (2014) 11-16;
kk) L. d. V. N. Caetano, et al., J Dermatol Sci, 88 (2017) 199-206;
ll) N. Uzunbajakava, et al., Biophys J, 84 (2003) 3968-3981;
mm) A. Zoladek, et al., J Raman Spectrosc, 42 (2011) 251-258;
nn) P. Piredda, et al., Anal Chem, (2015);
oo) J. W. Chan, et al., Biophys J, 90 (2006) 648-656;
pp) C. A. Patil, et al., Biomed. Opt. Express, 3 (2012) 488-502;
qq) H. Wang, et al., Sci. Rep., 3 (2013);
rr) M. B. Lopes, et al., Photochem Photobiol, 93 (2017) 613-618;
ss) J. Zhao, et al., Skin Research and Technology, 14 (2008) 484-492;
tt) Caspers P J, et al. *Automated depth-scanning confocal Raman microspectrometer for rapid in vivo determination of water concentration profiles in human skin*. J Raman Spectrosc 2000; 31:813-818;
uu) Caspers P J, et al. *In vivo confocal Raman microspectroscopy of the skin: noninvasive determination of molecular concentration profiles*. J Invest Dermatol 2001; 116:434-442;
w) Caspers P J, et al. *Monitoring the penetration enhancer dimethyl sulfoxide in human stratum corneum in vivo by confocal Raman spectroscopy*. Pharm Res 2002; 19:1577-1580.

All of these references are hereby incorporated herein by reference.

SUMMARY

This invention has a number of aspects, these include:
Apparatus for image guided targeting for optical spectroscopy measurements;
Methods for image guided targeting for optical spectroscopy measurements;
Apparatus for concurrent optical imaging and POI Raman spectroscopy;
Methods for concurrent optical imaging and POI Raman spectroscopy;

Apparatus for concurrent full field of view (FOV) optical imaging and region of interest (ROI) Raman spectroscopy; and Methods for concurrent full FOV imaging and ROI Raman spectroscopy.

One aspect of the invention provides a new type of integrated confocal Raman system which permits acquisition of confocal Raman signals at a specific point of interest (POI) under real-time full field of view (FOV) RCM guidance. The system has example application for ex vivo sample and in vivo tissue measurements. The system applies an optical isolator to separate the incident laser beam and the returning reflectance confocal beam.

Another aspect of the present invention provides devices and methods for detection and diagnosis of disease that applies RCM guidance for Raman spectroscopy of ex vivo samples and/or in vivo tissue measurements of a patient.

Another aspect of the present invention provides devices containing an optical Faraday isolator, arranged to separate light of an incident laser beam from light of a returning reflectance confocal beam.

Another aspect of the invention provides a system for image guided spectroscopy. The system may comprise a first light source arranged to emit first light into a first optical path that extends to an objective lens. The first optical path may include a scanner and an optical combiner between the scanner and the objective lens. The first optical path may further include an optical isolator comprising a Faraday rotator. The Faraday rotator may be located between the first light source and the scanner. The optical isolator may be configured to pass forward propagating light to the objective lens and to direct reverse propagating light to a light detector. The system may also comprise a second light source arranged to emit second light into a second optical path that extends to the objective lens. The second optical path may merge with the first optical path at the optical combiner. The system may also comprise a wavelength selector in the second optical path. The wavelength selector may be arranged to direct wavelengths corresponding to the second light after Raman shifting to a spectrometer.

In some embodiments the first light and second light have orthogonal polarization states at the optical combiner.

In some embodiments the optical combiner comprises a polarizing beam splitter.

In some embodiments the optical combiner comprises a polarizing bandpass filter having a cutoff wavelength between a wavelength of the second light and the wavelengths corresponding to the second light after Raman shifting.

In some embodiments the first light and the second light have the same wavelength.

In some embodiments the first light and the second light originate from a single laser. The system may comprise a beamsplitter arranged to separate a beam from the laser into the first light and the second light.

In some embodiments the beamsplitter is a polarizing beamsplitter. The system may also comprise a half-wave plate mounted for rotation between the laser and the beamsplitter.

In some embodiments the wavelength selector is located between the objective lens and the optical combiner.

In some embodiments the wavelength selector is located between the second light source and the optical combiner.

In some embodiments the system comprises one or more optical elements arranged to focus Raman shifted light directed by the wavelength selector into an optical fiber connected to deliver the Raman shifted light to the spectrometer.

In some embodiments the system comprises steering optics in the second light path. The steering optics may be configured to selectively position a point at which the second light is focused by the objective lens within a field of view of the objective lens.

In some embodiments the wavelength selector is between the steering optics and the second light source.

In some embodiments the system comprises an optical fiber bundle comprising a plurality of optical fibers arranged to carry Raman shifted light directed by the wavelength selector to the spectrometer. Each of the optical fibers may correspond to a location of the point at which the second light is focused by the objective lens within the field of view of the objective lens.

In some embodiments the wavelength selector is located between the objective lens and the optical combiner.

In some embodiments the system comprises a control unit connected to control the scanner to sweep a point at which the first light is focused by the objective lens in a scanning pattern over an imaging area and configured to process an output of the light detector to generate an image and to display the image on the display.

In some embodiments the control unit is configured to include in the displayed image indicia indicating a location within the imaging area at which the second light is focused by the objective lens.

In some embodiments the control unit is configured to monitor the image for changes indicating movement of the objective lens relative to a sample.

In some embodiments the control unit is configured to adjust the location within the imaging area at which the second light is focused by the objective lens to compensate for any detected movement.

In some embodiments the control unit is configured to generate an alert signal in response to detecting movement of the objective lens relative to the sample.

In some embodiments the control unit is configured to generate the image at a frame rate of at least 1 frame per second.

In some embodiments the system comprises a second scanner along the second optical path where the second scanner is operative to scan a point at which the second light is focused by the objective lens onto the sample in a scanning pattern comprising a plurality of locations in a region of interest.

In some embodiments the second scanner is operative to continuously scan the point at which the second light is focused between different locations of the plurality of locations.

In some embodiments the second scanner is between the second light source and the optical combiner.

In some embodiments the second scanner comprises an electronically controlled scanner.

In some embodiments the second scanner comprises a MEMS scanner, a resonant scanner or a pair of galvo scanners.

Another aspect of the invention provides a method for image guided spectroscopy. The method comprises imaging a sample by: emitting first light into a first optical path that extends to an objective lens, in the first optical path passing the first light in a forward direction through a Faraday rotator of an optical isolator to a scanner; and operating the scanner to scan a point at which the first light is focused by the objective lens over an imaging area on the sample, passing reflected light reflected by the sample back along the first optical path to pass through the Faraday rotator in a reverse direction and at an input polarizer of the Faraday rotator directing the reflected light to a light detector. The method also comprises, while imaging the sample, obtaining a Raman spectrum for a point on the sample by: directing second light into a second optical path that extends to the objective lens, the second optical path merging with the first optical path at an optical combiner; by the objective lens, focusing the second light onto the sample at the point; and collecting Raman scattered light from the point and directing the Raman scattered light back along the second optical path to a wavelength selector and by the wavelength selector directing the Raman scattered light to a spectrometer to obtain a Raman spectrum corresponding to the point on the sample.

In some embodiments the method comprises generating the first and second light by splitting a beam of light from a single laser.

In some embodiments the first light is cross polarized relative to the second light.

In some embodiments the method comprises processing an output of the light detector to yield an image of the imaging area of the sample and displaying on the image indicia indicating the point at which the second light is focused.

In some embodiments the method comprises monitoring the image to detect motion of the objective lens relative to the sample.

In some embodiments the method comprises adjusting a position of the point at which the second light is focused to compensate for any detected motion.

In some embodiments monitoring the image to detect motion of the objective lens relative to the sample comprises correlating frames of the image obtained at different times.

In some embodiments the method comprises generating an alert signal in response to detecting motion of the objective lens relative to the sample.

In some embodiments the monitoring of the image to detect motion is initiated upon acquisition of the Ramen spectrum being initiated.

In some embodiments the method comprises focusing the Raman shifted light directed by the wavelength selector into an optical fiber connected to deliver the Raman shifted light to the spectrometer.

In some embodiments the method comprises directing the second light to steering optics in the second light path and by the steering optics selectively positioning a point at which the second light is focused by the objective lens within a field of view of the objective lens.

In some embodiments the method comprises focusing Raman shifted light corresponding to each location of the point at which the second light is focused by the objective lens within the field of view of the objective lens into a different optical fiber of an optical fiber bundle comprising a plurality of optical fibers arranged to carry the Raman shifted light directed by the wavelength selector to the spectrometer.

In some embodiments the method comprises at the optical combiner passing light having a polarization state equivalent to the polarization state of the first light and blocking light having a polarization state equivalent to the polarization state of the second light or the Raman shifted light.

In some embodiments the method comprises at the optical combiner blocking light having a longer wavelength than a wavelength of the first light.

In some embodiments the method comprises adjusting an intensity of the first light relative to the second light by rotating a half-wave plate mounted for rotation between the laser and a polarizing beamsplitter.

In some embodiments the image is generated at a frame rate of at least 1 frame per second.

In some embodiments the method comprises focusing the second light onto the sample at a second point. The method may also comprise collecting Raman scattered light from the second point and directing the second Raman scattered light back along the second optical path to the wavelength selector and by the wavelength selector directing the second Raman scattered light to the spectrometer to obtain a second Raman spectrum corresponding to the second point on the sample.

In some embodiments the method comprises continuously scanning the point at which the second light is focused onto the sample over a region of interest of the sample.

In some embodiments scanning the point at which the second light is focused comprises operating an electronically controlled scanner in the second optical path to scan the point at which the second light is focused according to a scanning pattern of the region of interest.

In some embodiments the region of interest of the sample is a linear or a two-dimensional region of interest.

Further aspects and example embodiments are illustrated in the accompanying drawings and/or described in the following description. A person skilled in the art will realize that other embodiments of the invention are possible and that the details of the invention can be modified in a number of respects, all without departing from the inventive concept. Thus, the following drawings, descriptions and examples are to be regarded as illustrative in nature and not restrictive.

BRIEF DESCRIPTION OF THE DRAWINGS

The accompanying drawings illustrate non-limiting example embodiments of the invention.

FIGS. 4A and 4B are example RCM images of areas of a person's skin. FIG. 4C is a plot showing Raman spectra obtained for points of interest indicated in FIGS. 4A and 4B.

FIG. 6A is a schematic illustration showing a polarizing bandpass filter that may be used in place of a polarizing beam splitter to separate Raman shifted light from RCM light.

FIG. 6B shows an example transmission spectrum for a polarizing bandpass filter.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1:
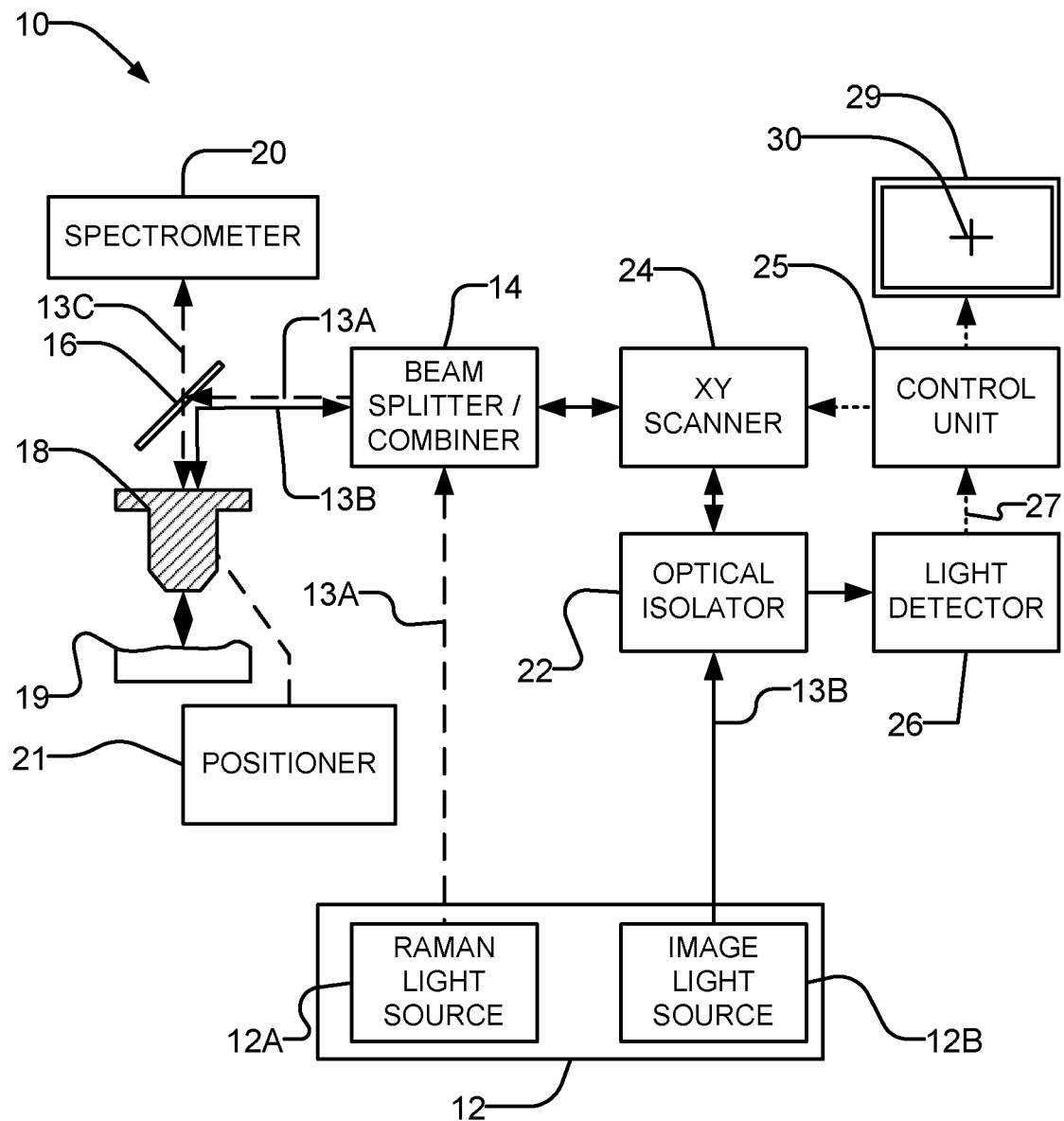
FIG. 1 is a schematic illustration showing an example architecture for a combined CRS and RCM system.

FIG. 1 is a simplified schematic illustration of a system 10 configured to perform Raman spectroscopy with image guidance. System 10 includes a light source 12. In the illustrated embodiment light source 12 comprises a light source 12A for Raman spectroscopy and a light source 12B for image guidance. These light sources may emit light having the same or different characteristics. In some embodiments the same light source is used to provide light for both Raman spectroscopy and image guidance (e.g., RCM). Providing one light source for both imaging modalities is advantageously simpler and potentially less expensive than providing separate light sources. For this reason, embodiments which use a single light source may be preferred in many applications.

Light source 12 emits light 13A which travels along a first optical path configured for Raman spectroscopy and light 13B which travels along a second optical path configured for imaging. The first and second optical paths merge at a beam combiner 14.

Light 13A is monochrome light. Light source 12 may include a laser that emits light 13A (or both light 13A and 13B). In the first optical path, light 13A travels to combiner 14 and continues to a wavelength selector 16 (e.g. a dichroic mirror) which directs light 13A into an objective lens 18. Light 13A passes through objective lens 18 to illuminate a subject 19. Subject 19 may comprise tissue in vivo or an ex vivo tissue sample, for example.

In the sample, some of light 13A is inelastically scattered and is therefore shifted to longer wavelengths relative to light 13A. Some of the wavelength-shifted scattered light 13C passes through objective lens 18. Light 13C passes through wavelength selector 16 to a spectrometer 20. Spectrometer 20 analyzes light 13C to detect Raman peaks, if any are present. As mentioned herein, the arrangement of Raman peaks provides a "fingerprint" that indicates the chemical composition of sample 19. Since changes in tissue pathology can be accompanied by chemical changes the Raman spectrum is a tool that may be applied to assess the pathology of tissue at a specific point in sample 19.

Advantageously the Raman spectrum may be obtained for a very small volume in sample 19 at the point where objective lens 18 focuses Raman light 13A. In some embodiments the location of the point where objective lens 18 focuses Raman light 13A is fixed relative to objective lens 18. In such embodiments the specific point in sample 19 to which the acquired Raman spectrum relates may be moved by changing the position of objective lens 18 relative to sample 19.

System 10 may include a positioner 21 (e.g. a piezoelectric positioner) operative to move objective lens 18 in two or three dimensions (e.g. XY or XYZ) to set locations for which Raman spectra are acquired. In some embodiments system 10 provides a mechanism for steering the point where objective lens 18 focuses Raman light 13A within a field of view enabled by objective lens 18. In such embodiments the specific point in sample 19 to which the acquired Raman spectrum relates may be moved by changing the position of objective lens 18 relative to sample 19 and/or steering the point of focus of Raman light 13A to a different location in the field of view of objective lens 18.

The mechanism for steering may comprise an electronically controlled scanner. The scanner may be electronically controlled to scan the point where objective lens 18 focuses Raman light 13A in a scanning pattern (e.g. a raster pattern) so that Raman light 13 is scanned over a region of interest within the field of view. A system as describes herein may include controls that allow a user to adjust a boundary of the region of interest (e.g. by changing the size, length, width, positions of vertexes, shape, aspect ratio, rotation angle or other features that define the boundary of the region of interest). Such adjustment bay be performed in real time while the field of view is being imaged as discussed herein.

Imaging light 13B passes through an optical isolator 22 to a 2D scanner 24 which directs light 13B into optical combiner 14. From optical combiner 14 light 13B is directed by wavelength selector 16 into objective lens 18. Light 13B is focused by objective lens 18 to a point on sample 19 that is determined by a setting of scanner 24. Scanner 24 is controlled by a control unit 25. Control unit 25 may, for example, cause scanner 24 to perform a raster scan at a desired resolution such that the point to which light 13B is focused by objective lens 18 sweeps out a pattern covering a field of view of sample 19.

Some of light 13B is scattered/reflected by sample 19 back into objective lens 18. That scattered/reflected light is directed by wavelength selector 16 back to optical combiner 14. Optical combiner 14 returns the scattered/reflected light to scanner 24 which sends the scattered/reflected light 13B back toward light source 12B.

Optical isolator 22 separates the scattered/reflected light 13B and directs the scattered/reflected light 13B to a light detector 26. Optical isolator 22 may, for example, comprise a Faraday isolator. Light detector 26 may be of any suitable design. For example, light detector 26 may be provided by an avalanche photodiode.

Light detector 26 produces an output signal 27 which indicates the intensity of the scattered/reflected light 13B. Signal 27 is provided to control unit 25. Control unit 25 generates an image of the field of view which is displayed on a display 29 in real time.

Display 29 includes indicia 30 which indicates the location in the displayed field of view at which Raman light 13A is focused onto sample 19. A user may observe the field of view on display 29, select specific points for which Raman measurements would be desirable, and adjust positioner 21 and/or a steering system for Raman light 13A (not shown in FIG. 1) to cause Raman light 13A to be directed to the desired location(s) on sample 19. Where system 10 is configured to obtain a Raman spectrum for a region of interest as opposed to a point, indicia 30 may indicate a boundary of the region of interest.

The architecture illustrated in FIG. 1 which uses an optical isolator to separate a returning RCM signal after descanning theoretically introduces no loss for both the illumination light 13B or the returning RCM signal. Many other configurations introduce losses in either or both of the illumination power or the confocal imaging signal detection.

Different types of positioner may be used for different applications. For example, a system for taking Raman spectra of points of interest on a patient's skin may include an xy translation stage operable to move the target skin under measurement in a lateral direction relative to objective lens 18. For in vivo skin measurement, a skin window equipped with a cover slip may first be attached to the skin surface. The skin window may couple magnetically to an XY stage. For example, the skin window may include a metal shape such as a ring attached to the skin with a suitable adhesive such as double-sided tape. This construction can suppress involuntary motion and the skin can also be stretched/moved by the stage in the horizontal plane.

Figure 1A:
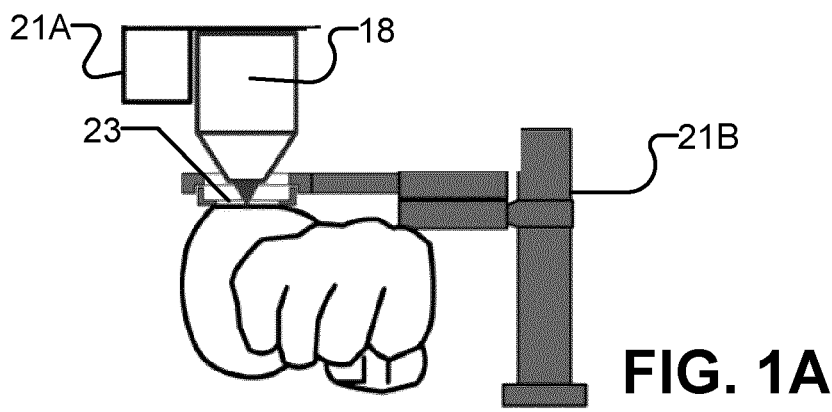
FIG. 1A illustrates an example positioner which may be used to obtain Raman spectra for points of interest on skin.

FIG. 1A shows an example arrangement being used to collect Raman spectra at points of interest on the skin of a person's arm. In FIG. 1A positioner 21 comprises an actuator 21A that is controllable to move objective lens 18 in a vertical (Z) direction and an XY stage 21B. Objective lens 18 views the person's skin through a window 23.

Systems with the general architecture illustrated in FIG. 1 may be implemented in a wide range of ways. Examples of different ways that such systems may be implemented will now be described. In the Figures illustrating these examples, functional components also illustrated in FIG. 1 are indicated with the same reference numbers used in FIG. 1. Such functional components may take different forms in different specific embodiments.

Figure 2:
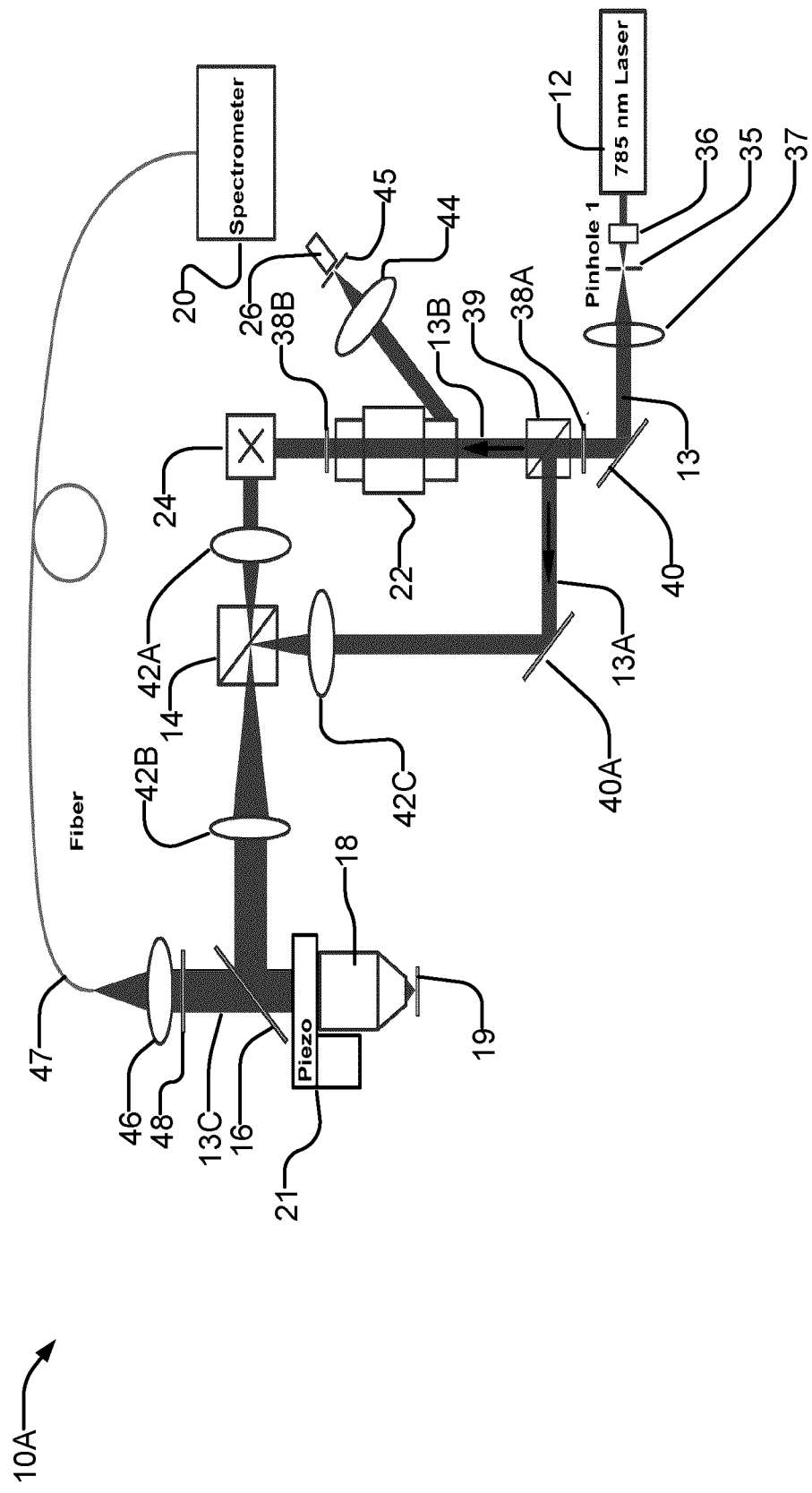
FIG. 2 is a schematic diagram showing an optical arrangement according to an example embodiment.

FIG. 2 is a schematic illustration depicting a system 10A which provides CRS with real-time RCM imaging monitoring. In this example, light for both CRS and RCM is provided from the same light source 12. The light source 12 may, for example, comprise a laser that emits light 13. For example, light 12 may comprise a continuous wave laser source that emits light at a suitable wavelength such as, for example, 785 nm. A prototype embodiment used a StarBright 785 XM™ laser available from StarBrightLaser AB (Sweden) for light source 12.

FIG. 2 illustrates a configuration in which:
light 13 from a single laser can be efficiently split and merged again to perform RCM and CRS at the same wavelength by using polarized beam splitters;
a polarization-dependent optical isolator 22 can efficiently separate a back-scattered/reflected RCM signal from a RCM illumination beam.

Light 13 from light source 12 is spatially filtered and collimated to provide a uniform beam of light 13. In the embodiment shown in FIG. 2 this is achieved by focusing light from light source 12 onto a spatial filter 35 (e.g. a pinhole such as a 10 µm diameter pinhole) with a lens 36 and collimating the light that has been spatially filtered by spatial filter 35 with a lens 37. The resulting beam of light 13 is then directed through a half-wave plate 38A into a beam splitter 39 that separates light 13 into CRS light 13A and RCM light 13B. An optional mirror 40 folds the path of light 13.

In the FIG. 2 embodiment, beam splitter 39 is provided by a polarized beam splitter cube. As a result, light 13A and 13B differ in polarization. A ratio of the intensities of beams 13A and 13B can be adjusted by rotating half-wave plate 38A.

Light 13B for RCM imaging passes through optical isolator 22. In the prototype embodiment, optical isolator 22 is provided by a Faraday isolator (model IO-5-780-HP available from Thorlabs). After optical isolator 22, light 13B passes through a second half-wave plate 38B and is scanned by a scanner 24. Scanner 24 may, for example, comprise a galvanometric scanner, a resonance scanner or the like.

The scanned beam 13B passes through optical combiner 14 which, in FIG. 2 is provided by a polarized beam splitter. Lens 42A concentrates the beam of light 13B onto optical combiner 24 and lens 42B expands the light output by optical combiner 24. The expanded light is relayed to the back aperture of objective lens 18 by wavelength selector 16. In the prototype embodiment wavelength selector 16 is provided by a dichroic beam splitter (RazorEdge™ Dichroic Beamsplitter LPD02-785RU-25, Semrock). Objective lens 18 focuses the light 13B onto sample 19.

In the prototype embodiment objective lens 18 was provided by a model LUMPLFLN60X/W, numerical aperture=1.0 objective lens available from Olympus Canada and was mounted on a piezo actuator (MIPOS 500 available from Piezo system Jena GmbH, Jena). The piezo actuator was operable to change the focal position of objective lens 18 in the z-direction.

Half-wave plate 38B and optical isolator 22 act in combination to separate the back reflected confocal signal from incoming light 13B. Optical isolator 22 may comprise a Faraday isolator. The Faraday isolator comprises a Faraday rotator located between an input polarizer and an output polarizer. The input and output polarizers have non-aligned polarization axes. For example, polarization axes of the input and output polarizers may be at an angle of 45 degrees to one another. For example, the input polarizer may pass light which is horizontally polarized and the output polarizer may pass light which is polarized at an angle of 45°. The Faraday rotator may rotate the polarization of light that passes through it by 45°.

In the FIG. 2 embodiment, light 13B emitted by beam splitter 39 may be horizontally polarized. When that light passes through the Faraday rotator the polarization direction is rotated by 45° and so the light 13B is transmitted by the output polarizer of optical isolator 22. Half wave plate 38B rotates the polarization of light 13B emitted from optical isolator 22 back to horizontal polarization. The back reflected light which makes up the RCM signal is also horizontally polarized. The polarization of the back reflected light is rotated by 45° when it passes through half wave plate 38B and is rotated by another 45° by the Faraday rotator. The back reflected light cannot pass through the input polarizer of optical isolator 22 because the confocal signal is now vertically polarized. The back reflected light is reflected out of optical isolator 22 at the input polarizer and is focused onto light detector 26 by lens 44.

In the prototype embodiment light detector 26 was provided by a model C10508 avalanche photodiode available from Hamamatsu Corp., Bridgewater, N.J. Lens 44 had a focal length of f=35 mm. A pinhole 45 may be placed in front of light detector 26 to reject out-of-focus signals. In the prototype embodiment pinhole 45 was a15 µm diameter pinhole.

In the prototype embodiment the RCM imaging process (controlling scanner 24 to sweep the point of focus of light 13B over a focal area of sample 19 and processing the output of light detector 26 to yield an RCM image) was controlled by a custom LabVIEW™ program. The imaging speed was one frame per second.

In the FIG. 2 embodiment, light 13A for point of interest (POI) CRS measurements is cross-polarized with the light 13B used for RCM imaging. For example, light 13A may be vertically polarized. Light 13A bypasses scanner 24 by way of mirror 40A and beam splitter 39, remains as a stationary beam, and is merged with scanning RCM imaging light 13B at light combiner 14. In the illustrated embodiment, light combiner 14 is provided in this embodiment by a polarizing beam splitter. Lens 42C concentrates light 13A onto optical combiner 14.

Light 13A is then relayed into objective lens 18 by wavelength selector 16. Light 13C which makes up the Raman signal passes through wavelength selector 16, is collected by lens 46 and is passed to an optical fiber 47 for delivery to spectrometer 20. In the prototype embodiment lens 46 had a focal length of f=75 mm. A long pass filter 48 may be provided to reduce the amount of light outside of a wavelength range of the desired Raman spectrum that is passed to spectrometer 20. In the prototype embodiment the long pass filter was a RazorEdge LP01-785RU-25 available from, Sem rock and optical fiber 47 was a 50 µm multimode fiber. In the prototype embodiment optical fiber 47 functions as a detection pinhole. A separate pinhole may optionally be provided to reject out of focus light.

In the prototype embodiment, spectrometer 20 was a custom-built spectrometer that includes a liquid nitrogen-cooled, back-illuminated, deep depletion CCD. The construction of the prototype spectrometer is described in detail in H. Wang, et al., Sci. Rep., 3 (2013).

Figure 3A:
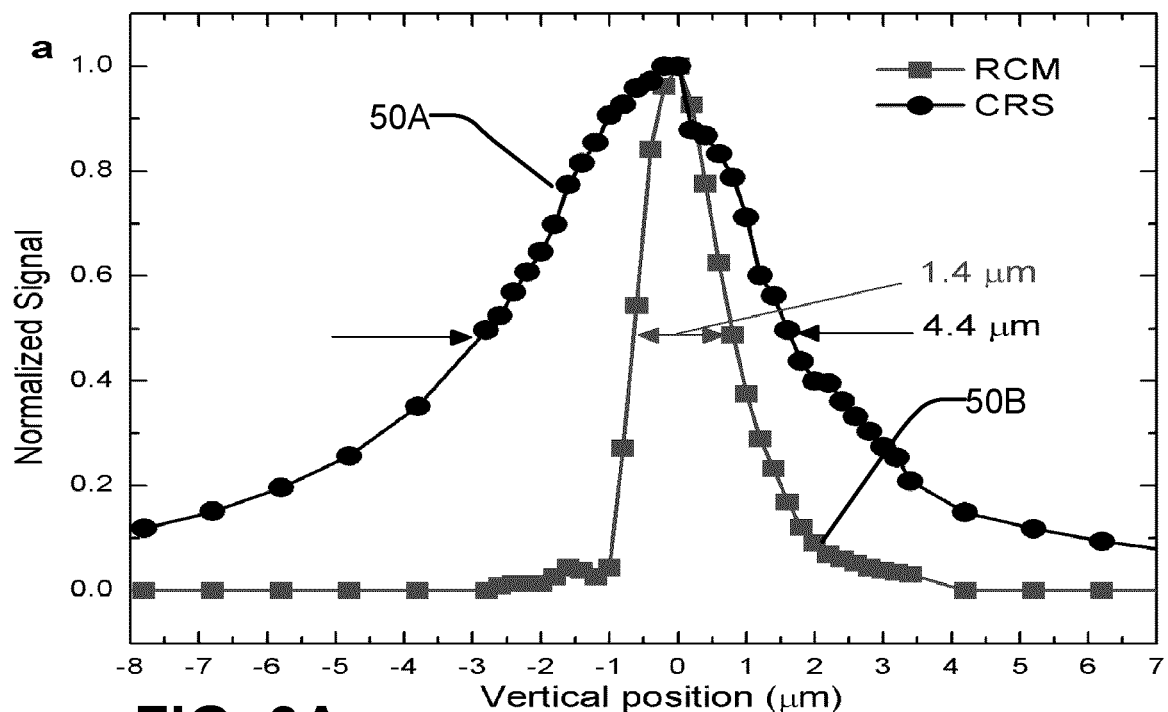
FIGS. 3A, 3B and 3C are graphs showing results of tests used to assess the resolution of a prototype system having the construction illustrated in FIG. 2.
Figure 3B:
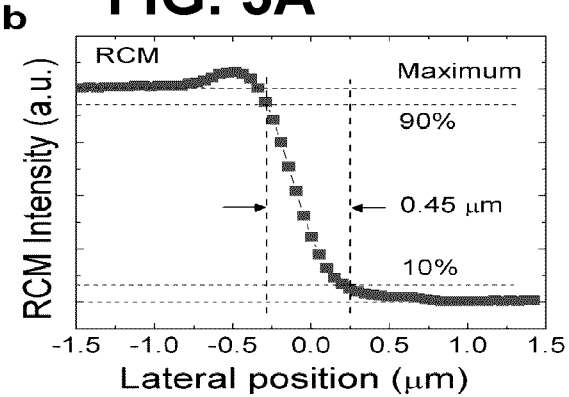
Figure 3C:
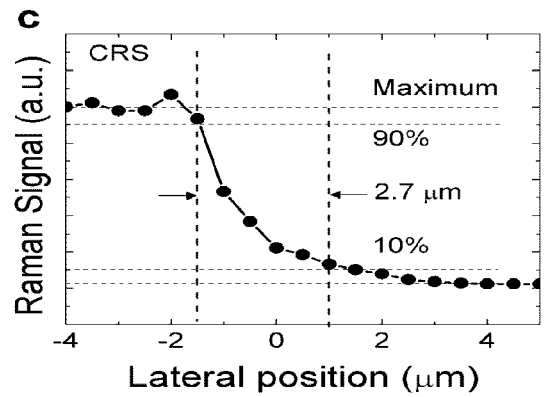

The performance of the prototype system was tested by measuring co-registration of the CRS and RCM channels by scanning a silicon wafer vertically. Signals from CRS and RCM were recorded simultaneously as objective lens 18 was moved vertically across the sample surface. FIG. 3A shows the normalized RCM signal 50B and CRS signal 50A (520 cm$^{-1}$ Raman peak of silicon) as a function of vertical position when the objective lens scans through the silicon wafer. The difference in vertical position of the two signal peaks is a measure of sectioning capabilities of the RCM and CRS channels. The close overlap of the two peaks indicates good co-registration (within 0.2 µm). The vertical resolutions of the CRS and RCM channels are found to be 4.4 µm and 1.4 µm respectively. The lateral resolutions for CRS and RCM were determined by scanning through the edge of a silicon wafer as shown in FIGS. 3B and 3C. The difference in lateral positions of 10% and 90% of the maximum signal is a measure of lateral resolution. The lateral resolutions of the RCM and CRS channels were found to be 0.45 µm and 2.7 µm respectively. Here again the 520 cm$^{-1}$ of silicon Raman is used as the CRS signal.

The prototype was tested to determine how much the light 13B used for RCM contributed to the Raman signal detected at light detector 26. For this experiment scanner 24 was controlled to scan RCM light 13B over a field of view having dimensions of 200 µm×200 µm. The optical power of both beams of light 13A and 13B were set to be the same. The beams making up light 13A and 13B were blocked separately.

In a one second exposure with beam 13B blocked, spectrometer 20 detected 55881 counts. With beam 13A blocked, spectrometer 20 detected only 101 counts. This shows that the contribution to the detected Raman spectrum resulting from light 13B is very small. A small contribution is expected because during Raman measurements, light 13A is always focused on the POI while light 13B is being scanned over the field of view. Light 13B can contribute to the Raman signal only when it is being scanned across the POI. Where light 13A and 13B have the same wavelength, even the very small amount of signal generated by the RCM beam will not distort the Raman signal.

The location of the POI on which light 13A is focused relative to the field of view scanned by light 13B may be determined by increasing the intensity of light 13A relative to light 13B and observing the location of a bright spot in the resulting RCM image. The location of the bright spot may be marked by a cross hair or other indicia 30 to be displayed in real time superposed with the RCM image. Indicia 30 may be used to place the POI for Raman spectroscopy at specific locations on a sample 19 and to ensure that the POI remains at the desired location on sample 19 during collection of the Raman spectrum.

The prototype system was used to examine human skin. FIGS. 4A and 4B respectively show in vivo RCM images of a sebaceous duct and an area of skin surrounding the sebaceous duct of FIG. 4A. Cross-hairs indicate the POI for confocal Raman measurement. The POI in FIG. 4A is inside the sebaceous duct. The POI in FIG. 4B is on skin epidermis on the left side of the sebaceous duct.

FIG. 4C shows confocal Raman spectra 51A and 51B respectively corresponding to FIGS. 4A and 4B. For illustration purpose, the spectra are shifted on the y-axis.

For the measurements in FIGS. 4A to 4C, laser power for the RCM channel and the CRS channel were both set to 25 mW. The integration time for confocal Raman measurements was 15 seconds. The imaging speed of the RCM channel was one frame per second. The FOV was 200 µm by 200 µm.

Raman spectra 51A and 51B both show major Raman bands at 855, 1002, 1128, 1445, and 1655 cm$^{-1}$. Raman spectrum 51A includes the characteristic Raman peaks 52 of palmitic acid which occur at wavenumber of 1296 cm$^{-1}$. This experiment demonstrates the ability of the real time image guided Raman spectroscopy as described herein to differentiate different tissues from one another.

Those of skill in the art will recognize a wide range of variations that may be applied to the system 10A of FIG. 2. For example, the resolution of each channel depends on a combination of objective lens 18, focusing lenses 44, 46, diameter of fiber 47 and/or the size of pinhole 45. The selections of these components may be modified for specific applications. Objective lens 18 may be integrated into probes of types suitable for accessing different body parts for in vivo confocal Raman measurement under real-time RCM imaging guidance.

Figure 5:
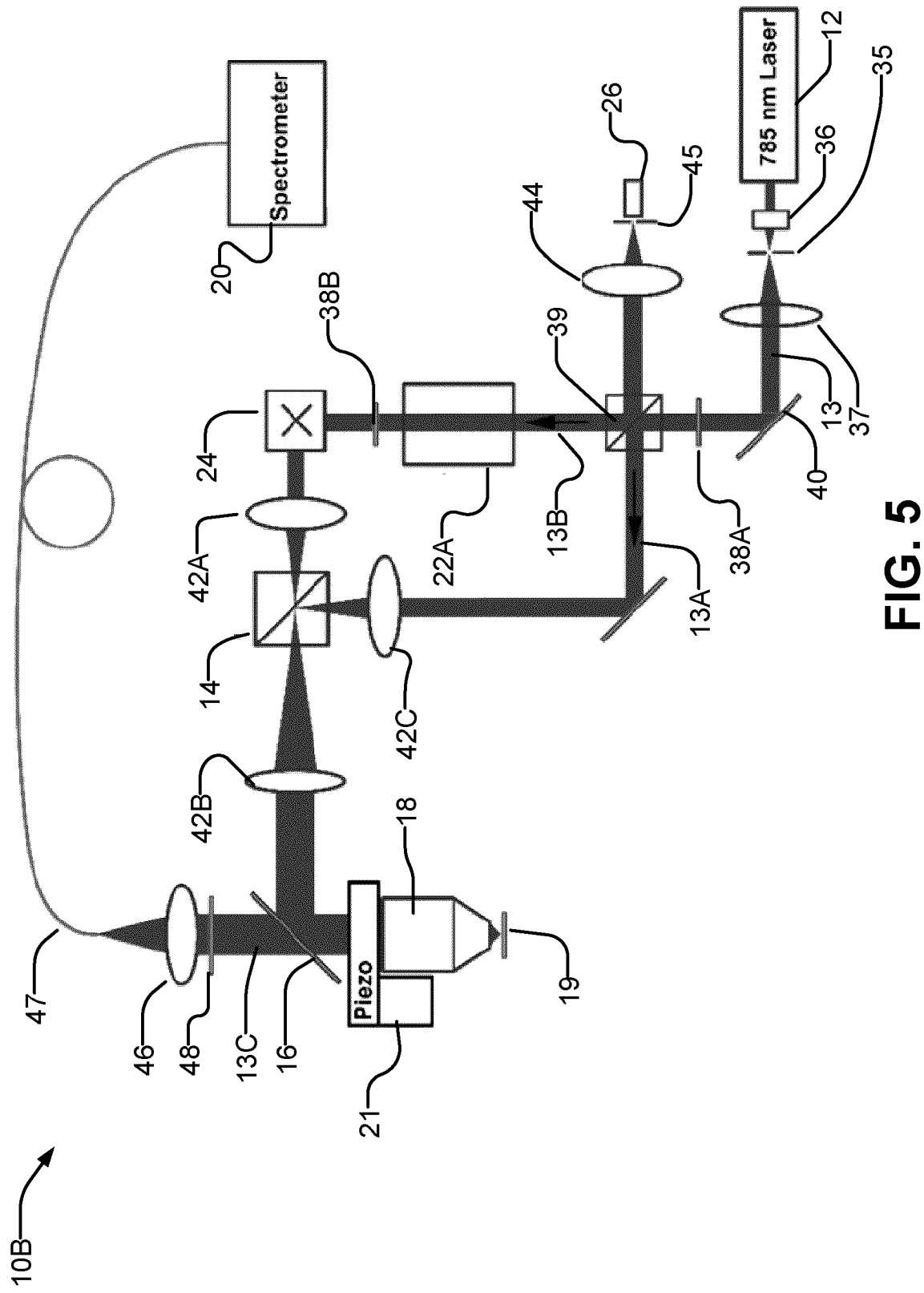
FIG. 5 is a schematic diagram showing an optical arrangement according to another example embodiment.

FIG. 5 illustrates a system 10B which is similar to system 10A of FIG. 2 except that optical isolation is provided by a Faraday isolator made up of a Faraday rotator in combination with polarizing beam splitters 14 and 39 which respectively act as the output and input polarizers of the Faraday isolator. The configuration of FIG. 5 is somewhat simpler than the configuration of FIG. 2 but can provide the same functionality.

One advantage of system 10A over system 10B is that using an optical isolator 22 having an input polarizer separate from other polarizers present in system 10A provides enhanced purification of the polarization of illumination laser beam 13B while the output polarizer of optical isolator 22 provides further rejection of non-confocal, multi-scattering photons which are depolarized.

Figure 6:
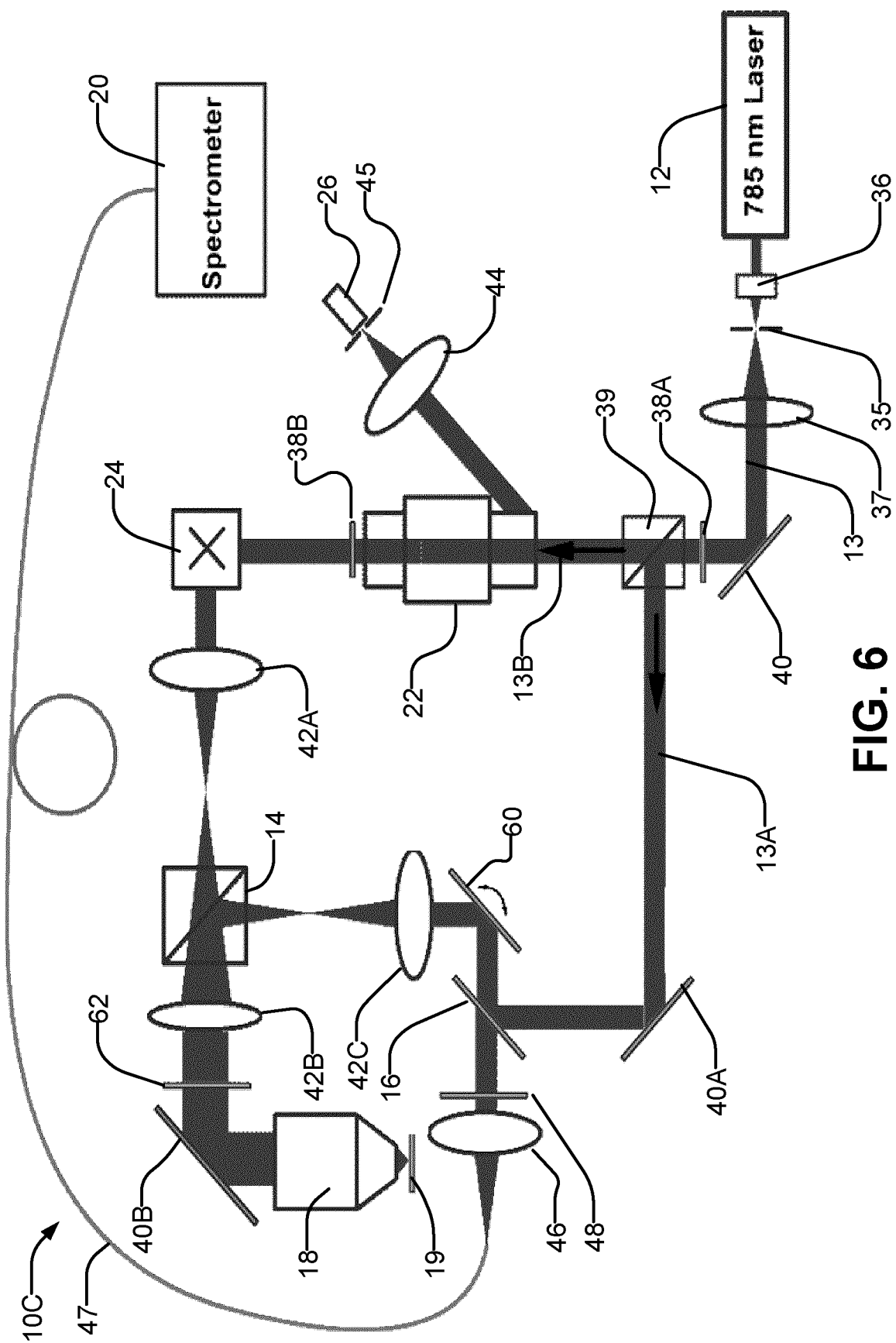
FIG. 6 is a schematic diagram showing an optical arrangement according to another example embodiment.

It is possible to provide a system as described herein wherein the POI for CRS is movable relative to the field of view for RCM. A schematic view of an example system 10C which is similar to system 10A of FIG. 2 but allows the POI for collecting Raman spectra to be moved relative to the field of view for RCM is shown in FIG. 6.

Parts of system 10C which have the same or similar functions to corresponding parts of systems 10, 10A and 10B are indicated using the same reference numbers.

System 10C differs from system 10A in that the optical path along which light 13A is relayed to light combiner 14 includes an adjustable mirror 60. Mirror 60 may be positioned manually and/or by way of an electronic positioning system (not shown). Mirror 60 may be tiltable in two directions and/or may comprise a pair of mirrors which are each adjustable to displace the POI for focusing light 13 and collecting Raman scattered light in different directions relative to the field of view of RCM imaging.

In system 10C, light 13A that is Raman scattered from sample 19 at the location of the POI and captured by objective lens 18 is directed back to mirror 60 by way of optical combiner 14, which is a polarizing beam splitter in this embodiment. As in system 10A, light 13A and 13B have orthogonal polarizations. Unlike system 10A, in system 10C the Raman signal detected is polarization dependent. The Raman signal is descanned by mirror 60 and passes to wavelength selector 16 which passes the Raman signal to optical fiber 47 by way of lens 46 and long pass filter 48.

System 10C allows confocal Raman measurement at an arbitrary point of interest in the field of view of RCM using a single laser source.

System 10C includes an adjustable quarter wave plate 62 which may be used to determine the focus position of the CRS beam in the field of view of RCM. When the optical axis of quarter wave plate 62 is aligned with the polarization of RCM light 13B the presence of quarter wave plate 62 does not affect RCM imaging.

To visualize location(s) of POI for CRS, quarter wave plate 62 may be rotated 45 degrees. In this rotated configuration, quarter wave plate 62 causes, both light 13A and light 13B that are incident on objective lens 18 to be circularly polarized. In this case the reflected RCM beam, after passing through quarter wave plate 62 again becomes vertically polarized (perpendicular to the polarization of incoming light. 13B). Therefore, most of the reflected RCM signal will not be detected at light detector 26. In this way, the focus position(s) of the CRS beam of light 13A on sample 19 will be shown as a bright spot in the field of view (dark background) of RCM. To change the location of a POI for Raman imaging one can adjust the angular position of mirror 60.

The Raman signal detected by system 10C is polarization dependent. Without quarter wave plate 62, only vertically polarized Raman signal is detected. When quarter wave plate 62 is present, the polarization of the Raman signal will be shifted first by quarter wave plate 62 and after that the vertical polarized component will be detected. Quarter wave plate 62 may be mounted so that it may be selectively removed from the optical path.

System 10C may be modified to allow collection of CRS from plural points and/or to allow collection of an integrated CRS signal from a linear or two-dimensional region of interest (ROI). For example, mirror 60 may be provided by a MEMS scanner, a resonant scanner, a pair of galvo scanners or another kind of electronically controlled scanner which is controlled to scan the point at which light 13A is focused onto sample 19 over a ROI and/or to step through collecting Raman spectra at plural discrete POIs.

System 10C may be modified to use an optical system in which optical isolator 22 is implemented as in system 10B.

System 10C may be modified to facilitate detection of the Raman signal in a way that is not polarization dependent by using a polarizing bandpass filter of a special design for optical combiner 14. The polarizing bandpass filter 14A (see e.g. FIG. 6A) should pass light 13B with the polarization state being used for RCM (e.g. horizontal polarization) in either direction and should block (reflect) both light at the wavelength of light 13B having other polarization states (in particular the polarization state of light 13A) as well as light that has been Raman shifted (i.e. light 13C). Suitable polarizing bandpass filters are available from Sem rock of Rochester USA.

As shown in FIG. 6B, the passband 55 of filter 14A may be selected to include the wavelength of light 13B and to exclude the wavelengths of Raman shifted light which has longer wavelengths (e.g. in region 56).

FIG. 6A illustrates a polarizing bandpass filter 14A.

Using a polarizing bandpass filter 14A as illustrated in FIG. 6A can double Raman signal collection efficiency by not limiting collected Raman signals to a single polarization state. At the wavelength of laser light source 12, filter 14A can separate or merge the light according to polarization. Raman signals outside of the passband 55 of filter 14A are all reflected for descanned detection and ultimate detection by spectrometer 20.

Figure 7:
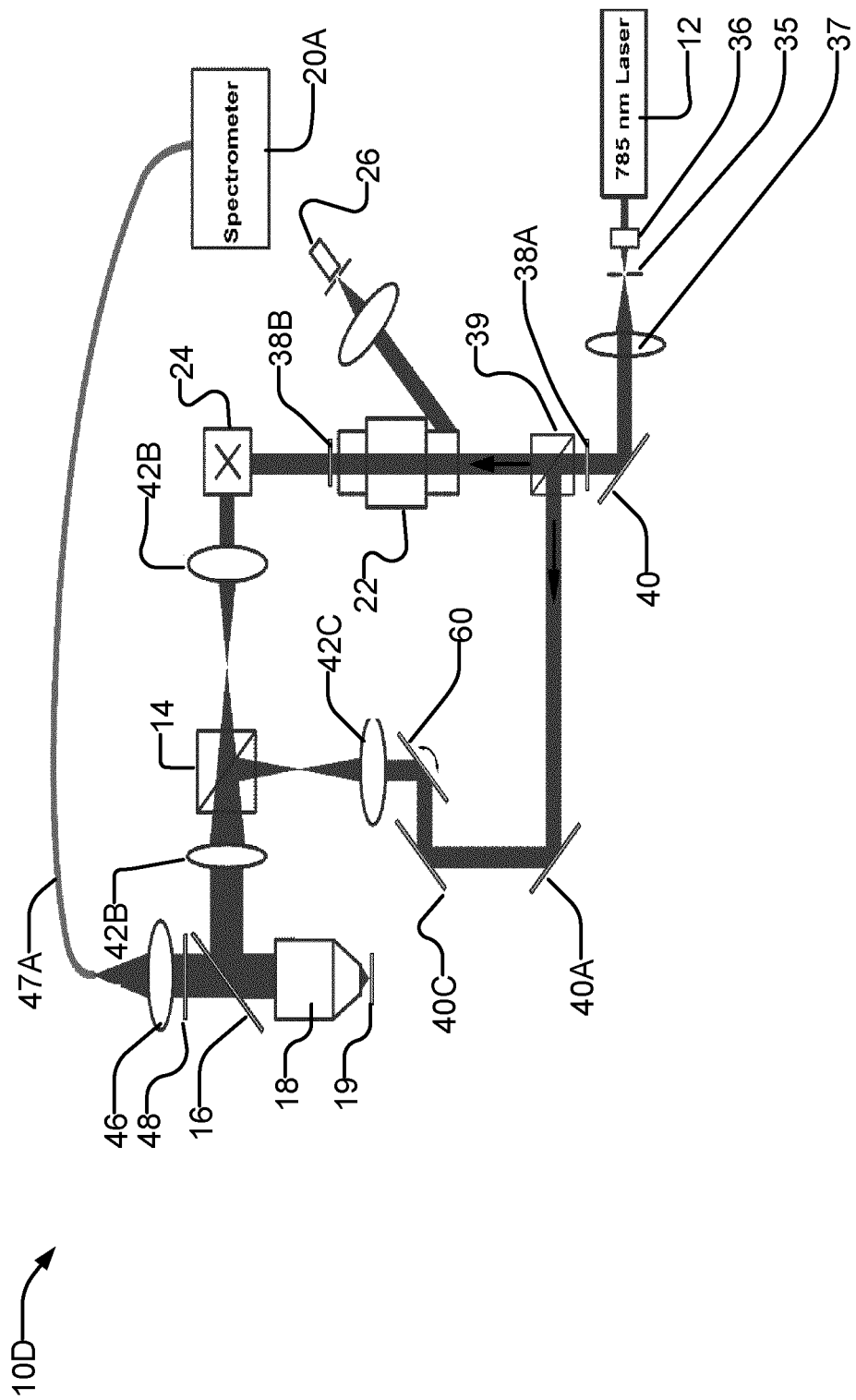
FIG. 7 is a schematic diagram showing an optical arrangement according to another example embodiment.

FIG. 7 shows a system 10D according to a further example embodiment. Parts of system 10D which have the same or similar functions to corresponding parts of systems 10, 10A, 10B or 10C are indicated using the same reference numbers.

System 10D is similar to system 10C except that it uses a fiber bundle to carry Raman scattered light to spectrometer 20A and it uses a spectrometer 20A that has multiple channels. System 10D can perform confocal Raman measurements at arbitrary points of interest in a field of view of RCM imaging. Detection of the Raman signal is not polarization dependent.

In system 10D, light 13A may be focused onto an arbitrary point of interest on sample 19 by adjusting mirror(s) 60. Raman scattered light 13C passes through wavelength selector 16 (due to having a different wavelength from light 13A) and is focused onto end 49A of fiber bundle 47A by lens 46.

Figure 7A:
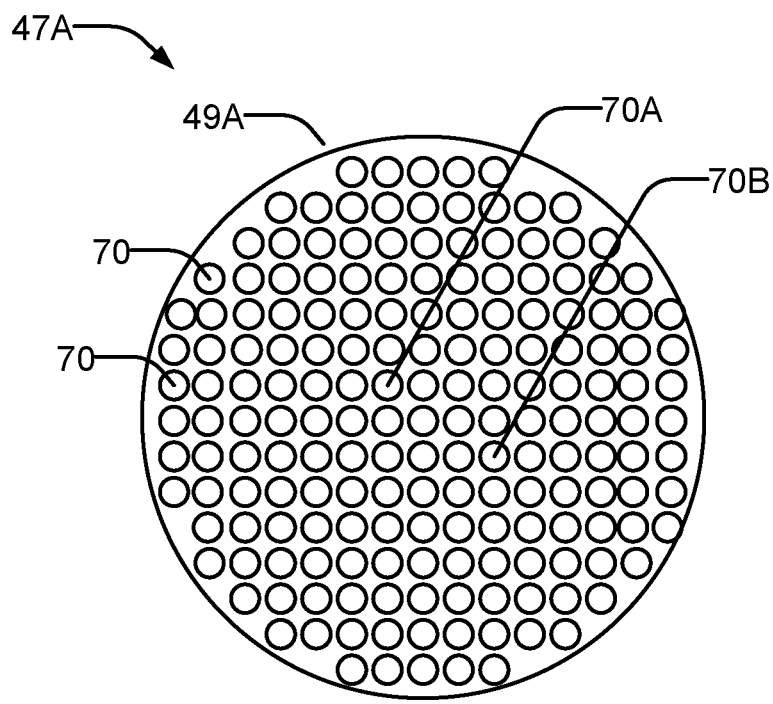
FIGS. 7A and 7B respectively show example configurations for fibers in input and output ends of a fiber bundle of the system shown in FIG. 7.

Fiber bundle 47A includes a large number of individual optical fibers 70 (e.g. 100 or more fibers 70). At end 49A, fibers 70 are arranged in a two-dimensional array (see FIG. 7A). The array may, for example, be round, rectangular, square or trapezoidal. Different locations on sample 19 correspond to locations of different ones of fibers 70. Light from one location on sample 19 may be focused onto a fiber 70A whereas light from a different location on sample 19 may be focused onto a fiber 70B.

Figure 7B:
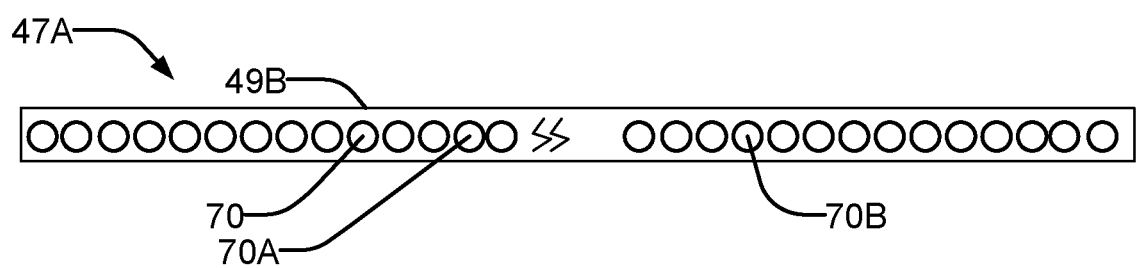

At the opposing end 49B of fiber bundle 47A where light is delivered to spectrometer 20A, fibers 70 are arranged in a one-dimensional array (e.g. a line) (see FIG. 7B). The Raman signal collected by any fiber 70 will therefore be delivered to a corresponding row of a light detector (e.g. a CCD) of spectrometer 20A. Since each fiber 70 corresponds to a position within the field of view of RCM images one can correlate a position of a POI to a CCD row index. This correlation may be done in advance. When mirror 60 directs light 13A to different positions on sample 19 the resulting Raman scattered light reaches spectrometer 20A by way of different fibers 70 of fiber bundle 47A. Light 13C received by way of the fiber 70 corresponding to the POI may be analyzed by spectrometer 20A to yield a Raman spectrum for the POI.

A limitation of system 10D is that the spatial resolution is limited by the number of fibers 70 and the number of columns of the CCD of spectrometer 20A.

System 10D may be modified to use an optical system in which optical isolator 22 is implemented as in system 10B.

In any of the embodiments described herein a controller may process real time RCM images to detect motion of an imaged sample relative to objective lens 18. Motion may be detected, for example, by performing correlations between frames obtained at different times. Upon detecting motion a controller may optionally generate an alarm signal indicating that motion has been detected. In some embodiments triggering for generating such signals is 'armed' in response to acquisition of a Raman spectrum being initiated. For example, a user may activate a control to acquire a Raman spectrum for a selected point of interest. If motion of the sample is detected during the Raman spectrum acquisition period (which may optionally be a predetermined time) then the alarm signal is generated. The user may then repeat acquisition of the Raman spectrum.

In embodiments which permit automatically controlled steering of the point of interest for acquiring a Raman spectrum, a system as described herein may automatically determine direction and magnitudes of motions of objective lens 18 relative to the sample and may automatically steer the CRS light to compensate for the motions.

In any of the embodiments described herein careful attention taken to avoid surface reflection in optical elements can help to avoid contaminating the confocal imaging signal. For example optical combiner 14 may be tilted slightly to prevent the reflection of its surface from entering the pinhole in front of light detector 26. Other details that may help to obtain good results include high-quality anti-reflection coatings or a polarizing plate beam splitter.

Those of skill in the art will understand that there are many alternative ways to direct light. For example, light may be guided to follow desired paths by using reflective elements such as mirrors, refractive elements such as prisms and/or optical waveguides. As another example, light may be focused using lenses, shaped mirrors, Fresnel elements or holographic elements. As another example, single optical elements may be replaced by groups of optical elements or vice versa. Those of skill in the art will recognize that the specific embodiments illustrated in the accompanying drawings may be varied in ways such as these without altering the principles of operation or overall architecture that distinguishes the present technology.

It can be seen that the embodiments described above each provide an optical path for imaging (e.g. RCM imaging) and an optical path for CRS. These optical paths may respectively be identified as "a first optical path" and "a second optical path" with no loss of generality. The imaging optical path and the CRS optical path merge at an optical combiner which is, for example, provided by a beam splitter (e.g. a polarizing beamsplitter), a polarizing bandpass filter of other suitable optical element or elements which merge light from the imaging and CRS optical paths. Each of the optical paths takes light from a light source 12 to an objective lens 18. The direction from the light source to the objective lens may be called a "forward" direction. Light propagating in the forward direction in either of the optical paths may be called "forward propagating light". Light that passes or has passed in the forward direction in the first optical path may be called "first light" and light that passes or has passed in the forward direction in the second optical path may be called second light. The direction from the objective lens to the light source in either optical path may be called a "reverse" direction. The source of the first light may be referred to as "a first light source" and the source of the second light may be referred to as "a second light source". The first and second light sources may be the same or distinct from one another. For example, a single component (e.g. a laser) may serve as both the first and second light sources. Light may interact with a sample by Raman scattering. The Raman scattering may shift wavelengths of the light by a Raman shift. Light that has undergone Raman scattering may be called "Raman scattered light".

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

A controller used in any embodiment of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Some aspects of the invention which involve computer instructions may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, aspects of the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A system for image guided spectroscopy, the system comprising:
   a first light source arranged to emit first light into a first optical path that extends to an objective lens, the first optical path including a scanner and an optical combiner between the scanner and the objective lens, the first optical path further including an optical isolator comprising a Faraday rotator, the Faraday rotator located between the first light source and the scanner, the optical isolator configured to pass forward propagating light to the objective lens and to direct reverse propagating light to a light detector;
   a second light source arranged to emit second light into a second optical path that extends to the objective lens, the second optical path merging with the first optical path at the optical combiner and the first light and the second light having orthogonal polarization states at the optical combiner; and
   a wavelength selector in the second optical path, the wavelength selector arranged to direct wavelengths corresponding to the second light after Raman shifting to a spectrometer;
   wherein the first light and the second light have the same wavelength and originate from a single laser and the system comprises a beamsplitter arranged to separate a beam from the laser into the first light and the second light.

2. The system according to claim 1 wherein the optical combiner comprises a polarizing beam splitter.

3. The system according to claim 1 wherein the optical combiner comprises a polarizing bandpass filter having a cutoff wavelength between a wavelength of the second light and the wavelengths corresponding to the second light after Raman shifting.

4. The system according to claim 1 wherein the beamsplitter is a polarizing beamsplitter and the system comprises a half-wave plate mounted for rotation between the laser and the beamsplitter.

5. The system according to claim 1 comprising one or more optical elements arranged to focus Raman shifted light directed by the wavelength selector into an optical fiber connected to deliver the Raman shifted light to the spectrometer.

6. The system according to claim 1 comprising steering optics in the second light path, the steering optics configured to selectively position a point at which the second light is focused by the objective lens within a field of view of the objective lens.

7. The system according to claim 6 comprising an optical fiber bundle comprising a plurality of optical fibers arranged to carry Raman shifted light directed by the wavelength selector to the spectrometer wherein each of the optical fibers corresponds to a location of the point at which the second light is focused by the objective lens within the field of view of the objective lens.

8. The system according to claim 6 wherein the steering optics comprise an electronically controllable scanner and the system comprises electronics configured to control the electronically controllable scanner to scan a portion of the field of view according to a scanning pattern such that the spectrometer obtains a Raman spectrum for the portion of the field of view.

9. The system according to claim 8 comprising controls for adjusting a boundary of the portion of the field of view in real time while concurrently imaging the field of view.

10. The system according to claim 1 comprising a control unit connected to control the scanner to sweep a point at which the first light is focused by the objective lens in a scanning pattern over an imaging area and configured to process an output of the light detector to generate an image and to display the image on the display.

11. The system according to claim 10 wherein the control unit is configured to include in the displayed image indicia indicating a location within the imaging area at which the second light is focused by the objective lens.

12. The system according to claim 10 wherein the control unit is configured to monitor the image for changes indicating involuntary movement of a sample relative to the objective lens.

13. The system according to claim 10 wherein the control unit is configured to adjust the location within the imaging area at which the second light is focused by the objective lens to compensate for any detected movement of a sample.

14. The system according to claim 10 wherein the control unit is configured to generate an alert signal in response to detecting involuntary movement of a sample relative to the objective lens in the imaging area.

15. The system according claim 10 wherein the control unit is configured to generate the image at a frame rate of at least 1 frame per second.

16. The system according to claim 1 comprising a second scanner located in the second optical path and operative to scan a point at which the second light is focused by the objective lens in a scanning pattern comprising a plurality of locations in a region of interest.

17. The system according to claim 16 wherein the second scanner is operative to continuously scan the point at which the second light is focused between different ones of the plurality of locations.

18. The system according to claim 16 wherein the second scanner comprises an electronically controlled scanner.

\* \* \* \* \*